United States Patent
Cortelezzi

(10) Patent No.: US 6,764,692 B1
(45) Date of Patent: Jul. 20, 2004

(54) METHOD TO TREAT LAMINITIS AND REDUCE DIETARY INTAKE FOR HORSES

(76) Inventor: Carlos Cortelezzi, 1547 NW. 29 St., Miami, FL (US) 33142

( * ) Notice: Subject to any disclaimer, the term of this patent is extended or adjusted under 35 U.S.C. 154(b) by 3 days.

(21) Appl. No.: 10/228,500

(22) Filed: Aug. 27, 2002

(51) Int. Cl.[7] .................. A61K 33/00; A61K 33/04; A61K 33/06; A61K 33/14; A61K 33/16; A61K 33/18; A61K 33/22; A61K 33/24; A61K 33/26; A61K 33/30

(52) U.S. Cl. .................. 424/442; 424/439; 424/125; 424/600; 424/601; 424/602; 424/603; 424/604; 424/605; 424/606; 424/617; 424/618; 424/620; 424/621; 424/629; 424/630; 424/638; 424/639; 424/641; 424/643; 424/646; 424/649; 424/650; 424/651; 424/652; 424/653; 424/654; 424/655; 424/657; 424/663; 424/667; 424/673; 424/677; 424/682; 424/702; 424/703; 424/704; 424/705; 424/718; 424/719; 424/722; 424/723; 424/724; 424/DIG. 6; 514/63; 514/64; 514/75; 514/492; 514/493; 514/494; 514/495; 514/498; 514/499; 514/500; 514/501; 514/502; 514/503; 514/504; 514/505; 514/836; 514/886; 514/905; 514/909; 514/910; 514/970; 426/2; 426/74

(58) Field of Search .................. 424/439, 125, 424/442, 600–606, 617–618, 620–621, 629–630, 638–639, 641, 643, 646, 649–655, 657, 663, 667, 673, 677, 682, 702–705, 718–719, 722–724, DIG. 6; 426/2, 74; 514/63, 64, 75, 492–496, 498–505, 836, 886, 905, 909, 910, 970

(56) References Cited

U.S. PATENT DOCUMENTS 6,299,886 B1 * 10/2001 Piper .................. 424/400

FOREIGN PATENT DOCUMENTS

WO     00/48613    * 8/2000

OTHER PUBLICATIONS

VETU Abstract, accession No. 1999–61341 (1999).*
Chemical Abstracts 122:131771 (1995).*
Nocek, J.E. et al., "Digital Characteristics in commercial dairy herds fed metal–specific amino acid complexes," Journal of Dairy Science, vol. 83(7), pp. 1553–1572 (2000).*
VETU Abstract, accession No. 1985–62138 (1985).*
WPIDS (Derwent) Abstract, accession No. 1995–083916 (1995).*

* cited by examiner

Primary Examiner—John Pak
(74) Attorney, Agent, or Firm—Albert Bordas; Jesus Sanchelima

(57) ABSTRACT

A method of treating laminitis in a horse is disclosed, comprising administering to the horse a naturally chelated trace mineral composition; promoting healthy skin, hair and hoof tissue. A method of reducing dietary intake is also disclosed, comprising administering to a horse in need thereof, effective amounts of a naturally chelated trace mineral composition. A method of preparing the chelated trace mineral composition from ocean seabed rock is further disclosed, as well as the chelated trace mineral composition.

6 Claims, No Drawings

METHOD TO TREAT LAMINITIS AND REDUCE DIETARY INTAKE FOR HORSES

BACKGROUND OF THE INVENTION

1. Field of the Invention

The present invention relates to methods for treating horses, and more particularly, to administering mineral supplements for treating laminitis while reducing dietary intake.

2. Description of the Related Art

Many methods for treating horses have been developed in the past. None of them, however, include naturally chelated trace minerals.

Laminitis is defined as an inflammation of the sensitive laminae of the hoof, especially in horses. Laminitis is also defined as the inflammation of the laminae or fleshy plates along the coffin bone of a horse; and yet further defined as inflammation of the laminated tissue that attaches the hoof to the foot of a horse, which allows on a chronic stage the rotation of the coffin bone, also called founder.

Presently, trace minerals, sold as a premix, are utilized for animals. However, premixed trace minerals are limited, in that they do not contain natural compositions that contain heavy metals in concentrations as little as parts per million, with diluted gases and most of the known oligo-elements.

Natural compositions are recognized in the body as catalytic agents, which help dissolve matter during the digestion process that are not usually dissolved. This process protects the body from effects of heavy indissoluble molecules that travel through different systems, arriving at the perypheric blood vessels, where they cause toxicity. Toxicity kills cells of the vessels and cause necrosis or death of surrounding tissues, which is what causes inflammation and death of the laminae of the hoof. This condition allows for the coffin bone to rotate, developing founder.

Treating horses also requires a healthy dietary intake. Simply from an economic viewpoint, it is desired to promote and maintain the health of horses, efficiently with regard to cost of dietary intake.

There are no similar methods to prevent and treat laminitis, and reduce dietary intake to the best of applicant's knowledge, that use naturally chelated trace minerals.

SUMMARY OF THE INVENTION

Trace minerals, and chelated trace minerals in particular, have incredible effects over different areas of the body of a horse. Such effects, include: anti-inflammatory actions, enhancing effects over absorption capabilities of the digestive tract, mineralizing effects over depleted bone structures, antioxidant effects, and antitoxic effects that prevent many everyday food poisonings and related sequels of the kind that end up causing the frequently seen laminitis.

These chelated trace minerals belong to a group of montmoryllonites, and are found as naturally occurring compounds that originated from fossilized animals, plankton, algae and plants from Ancient Ocean seabed. The naturally occurring compounds are found today as rocks.

More specifically, the instant invention is a method of treating laminitis in a horse in need thereof. It comprises administering to the horse an effective amount of a chelated trace mineral composition for promoting healthy hoof tissue. The chelated trace mineral composition is administered with a dose of approximately 2 ounces, twice a day, for a period of 20 days, while maintaining a protein content of a horse diet to approximately 9%–10% of a total dietary intake per day. In the preferred embodiment, the chelated trace mineral composition is administered orally.

The instant invention is also a method of reducing total dietary intake per day of a horse in need thereof. It comprises administering to the horse an effective amount of a chelated trace mineral composition for promoting a reduction of daily grain intake. The chelated trace mineral composition is administered with a dose of approximately 2 ounces, once a day, for a period of 20 days, and with a dose of approximately 1–2 ounces per day after completing said period of 20 days, while maintaining a protein content of a horse diet to approximately 9%–10% of a total dietary intake per day. In the preferred embodiment, the chelated trace mineral composition is administered orally.

It is therefore one of the main objects of the present invention to provide methods of preventing and treating laminitis in horses; promoting healthy skin, hair, and hoof tissue, comprising administering to horses chelated trace minerals.

It is another object of this invention to provide a method of reducing grain intake for horses; comprising administering to horses chelated trace minerals.

It is still another object of the present invention to provide a composition suitable for treating laminitis and/or reducing grain intake for horses.

Yet another subject matter of the invention is a method of preparing a chelated trace mineral composition from ocean seabed rocks, comprising:

A) collecting ocean seabed rocks;
B) removing a superficial layer of crust from said ocean seabed rocks to produce a harvestable portion;
C) breaking-down said harvestable portion with a rototiller machine to produce a mixture of medium to small rocks, together with different fractions of smaller rocks and dust, producing a first matter;
D) providing a chelated trace mineral extract from said first matter with a screening process, producing processed matter;
E) drying and/or re-mixing said processed matter if necessary, by filtrating said processed matter produced in step D) with mesh material an additional time; and
F) preparing a chelated trace mineral composition for packaging, having a predetermined average chelated trace mineral content.

It is yet another object of this invention to provide such a method and composition that is inexpensive to manufacture and maintain while retaining its effectiveness.

Further objects of the invention will be brought out in the following part of the specification, wherein detailed description is for the purpose of fully disclosing the invention without placing limitations thereon.

DETAILED DESCRIPTION OF THE PREFERRED EMBODIMENT

The present invention improves the overall health of horses, and more specifically, treats and prevents laminitis, and reduces the dietary intake necessary to promote and maintain overall health.

Without being bound by any theory, the present inventor believes that naturally chelated trace minerals, harvested from ocean seabed rock, makes their rare ingredients (such as heavy metals, diluted gases and oligo-elements), easily absorbable, causing no toxicity. High amounts of silicone, helps regenerate cell membranes all over the body of the horse, increasing the speed of healing of wounds and inflammations. The present inventor further believes that the present invention acts as a powerful antioxidant, anti-inflammatory and antitoxic agent; working as an anti-arthritic, it increases the speed of growth of the skin, hair, and hoof tissues.

Again, without being bound by any theory, the present inventor believes that the basic damage of the laminar structure originates from an endo-toxic origin. The present inventor believes the present invention is a potent anti-toxic and antioxidant, inactivating several common toxins found in horse food, such as aflatoxins, thus protecting the capillaries of the laminae and preventing inflammatory damage known as laminitis. The present inventor believes the invention disrupts heavy, toxic molecule formation, that otherwise cause damage to the blood vessels that conform the laminae. This occurs even with aflatoxin levels (fungus) of more than 40 parts per billion, when typically, standards of no more than 20 parts per billion are allowed. Thus, the prevention of laminitis is promoted.

Regarding the reduction of dietary intake, without being bound by any theory, the present inventor believes that components of the chelated trace mineral composition allow for the absorption of some lignified portions of forage. This results in converting them into digestible particles, allowing additional food to be eliminated by the intestine as processed, resulting in less food (such as grain) needed per day to maintain the same body weight.

In the present method for the treatment of laminitis, the chelated trace mineral composition, the mineral content seen in chart 1, is administered with a dose of approximately 2 ounces, twice a day, preferably orally, for a period of 20 days. During the period of 20 days, it is necessary to maintain a protein content of the horse's diet to approximately 9%–10% of the total dietary intake per day. A 12% or greater protein content of the total dietary intake per day will negate the effectiveness of the instant method, because an excessive production of fermented metabolites will enter the blood stream of the horse, through the intestinal walls; causing a gradual endotoxemic effect that worsens the laminitic condition.

Approaching the end of the period of 20 days, improvements are noticeable. Improvements are realized in the condition of hair, together with skin and nail tissue (hooves). Old hair will fall off, and be replaced with new hair. Growth of the sole is noticeable and the development of an elastic, harder, new tissue is observed.

No other known hoof enhancers, such as the biotin or methionine type, are used with the instant method. However, it is recognized that combination of either enhancer with the instant method will also produce beneficial results.

Upon completion of the above-described administration over the period of 20 days, a better displacement of a horse is realized. A visible improvement of the laminitic condition is realized, wherein horses, not capable of walking may do so after the treatment is complete. The present invention increases the speed of growth of the hoof with poor circulation, by as much as one and one-quarter inch in a period of six weeks, when normal growth is typically one-third of this. New sole grows in areas that protect the coffin bone from contact with the ground. The present invention may also be used as a detox-factor to prevent laminitis. This allows cured horses to live a life that allows them to reproduce and be of some service, if feasible.

Upon completion of the treatment over a period of one year, rotations of the coffin bone may be prevented all together if the supplementation is regularly continued. Laminitis cases become very infrequent, with the exception of major changes in food components taking place, such as during changes of seasons; rainy season to dry or vice-a-versa, with its consequent increase of aflatoxins and other toxics.

During experimentation, 18 foundered horses were identified from a population of 150 in stalls, accounting for over 10 %. Some horses had aggressive founder signs; with soles deformed, perforated, and having a multitude of abscesses. In some cases, the founder was so developed that some horses had a surgical procedure performed by tenectomy, to alleviate the pull of the deep flexor tendon that rotated the coffin bone. This procedure requires the cutting and extraction of the deep flexor tendon. Still other horses had a demineralizing process, causing their coffin bones to weaken, manifesting unbearable pain. The experimentation realized a more than 10% incidence rate to zero rotations. With the present invention, horses that are very lame, may stand in ten days in some cases, after being unable to stand for periods of a month. Shortly thereafter, horses may walk.

Additionally, improvements in coffin bone density were observed through X-rays, where depleted bones were remineralized, thus strengthening areas sensitive to osteoporosis. The same could be said for those horses that were diagnosed with arthritis in the hocks (bone spavin). These tended not to show the symptoms of the arthritis as much, so long as they were treated with the present invention. Additional benefits also include the maintenance of osmotic pressure of cells, avoiding dehydration, and also acting as an anti-stress factor.

Other desirable effects of the administration of the chelated trace mineral composition, is the reduction in the amount of grain administered daily to horses. Since components of the chelated trace minerals allow for the absorption of some lignified portions of grass (forage), converting them into digestible particles, a lot of the food normally eliminated by the intestine as unprocessed is used by the body, resulting in less food needed per day, to maintain the same body weight. Experimentation resulted in a daily reduction of grain by 20% of the dietary intake after a few months of administration. The present invention allows for savings of 20% in the purchase of grain, which translates into thousands of dollars. Specifically for adult horses, approximately two pounds of grain may be given twice daily. Furthermore, the present invention generates a wide variety of enzymes that aid in the digestive process.

As a dietary supplement, the chelated trace mineral composition is administered with a dose of approximately 2 ounces, once a day, preferably orally, for a period of 20 days. During the period of 20 days, it is necessary to maintain a protein content of the horse diet to approximately 9%–10% of the total dietary intake per day. Similarly as described above, a 12% or greater protein content of the total dietary intake per day will negate the effectiveness of the instant method because an excess of protein will produce un-degraded portions of the ration, to ferment and cause the absorption of toxins derived from that fermentation through the intestinal wall and to the blood stream, causing endotoxemy. After completing the period of 20 days, the chelated trace mineral composition is administered with a dose of approximately 1–2 ounces per day, depending on the size of the horse. The protein content of the diet should be maintained approximately at 10%, especially for adult horses.

In addition, the present invention oxygenates cells, increasing stamina for the horse, which in turn increases the overall performance and reduces fatigue.

The present invention also includes a method of preparing a chelated trace mineral composition from ocean seabed rocks, comprising:

A) collecting ocean seabed rocks;

B) removing a superficial layer of crust from said ocean seabed rocks to produce a harvestable portion;

C) breaking-down said harvestable portion with a roto-tiller machine to produce a mixture of medium to small rocks, together with different fractions of smaller rocks and dust, producing a first matter;

D) providing a chelated trace mineral extract from said first matter with a screening process, producing processed matter;

E) drying and/or remixing said processed matter if necessary, by filtrating said processed matter produced in step D) with mesh material an additional time; and F) preparing a chelated trace mineral composition for packaging, having a predetermined average chelated trace mineral content.

Step A) of the method includes, collecting ocean seabed rocks with a front-loading tractor having a roto-tiller rear unit.

Step B) of the method includes, removing the superficial layer of crust by removing six to twelve inches of outer matter and setting it aside as waste with the front-loader. The resulting matter is defined as the harvestable portion.

Step C) of the method includes, breaking-down the harvestable portion with a roto-tiller machine, in increments of six to twelve inches at a time. The product of this step is defined as a first matter, being a mixture of medium to small rocks, together with different fractions of smaller rocks and dust.

Step D) of the method includes, providing a chelated trace mineral extract from the first matter ocean seabed rocks with a screening process, wherein three different types of extracted products are obtained from a three-layer elliptical screener.

After preparing the first matter, a second front-loading tractor picks it up from the ground and transports it to a hopper, which funnels the first matter to a first conveyor belt, transporting it to a front portion of the elliptical or circular motion screener.

A first layer of screen mesh has a measurement of ⅛ inch, which separates the bigger rocks from the rest of the first matter, up to ⅛ inch. A second layer of screen mesh has a measurement of 20 mesh, which recovers all particles of the first matter with a measurement of ⅛ inch, and eliminates them independently through a first spout. A third layer of screen mesh has a measurement of 30 mesh size, which eliminates the majority of the 20 mesh size first matter through a second spout, and screens the 30 mesh size particles of first matter through a third spout, completing the screening process, and discharging processed matter.

The third layer of screen mesh (30 mesh) allows particles of first matter up to a size of 600-mesh to trespass through, which is an important fraction of the finished product because the smaller the size of the particle of matter, the larger absorption ratio at the intestinal level.

Step E) of the method includes, drying and/or re-mixing if necessary. This step comprises filtrating the processed matter produced in step D) with mesh material an additional time. The processed matter is collected on second and third conveyor belts and transported to two different areas for further processing. Processed matter identified as rocks and that of ⅛ inch, is collected through the second conveyor belt and transported to a roller-mill with a size production of 16 mesh. The roller mill pulverizes the processed matter identified as rocks and that of ⅛ inch to a measurement of less than 16 mesh, with a very low production of heat. This process prevents particles of the chelated trace minerals, defined as thicker and amounting to approximately 20% of the total chelated trace minerals, to loose diluted gases by virtue of the use of low-heat generating processing techniques. Processed matter identified as that of 20 mesh, 30 mesh and smaller, are collected by a third conveyor belt and re-directed to the front of the elliptical screener.

Step F) of the method includes, preparing a chelated trace mineral composition for packaging, having a predetermined average chelated trace mineral content, as seen in chart 1.

Chelated trace mineral compositions of 20 to 30 mesh are packed for horses and animals defined as pets. Chelated trace mineral compositions of 30 mesh to 600 mesh are packed for human use. All other remains of processed matter may be reprocessed with the above-described steps and packed for cattle, poultry and pork use.

The specifications of an example chelated trace mineral composition prepared according to the described method is seen in chart 1 below. The mineral contents listed are an average, and may fluctuate, as it is noted that they are derived from a naturally occurring ocean seabed rock basin.

CHART 1

| | | | | | |
|---|---|---|---|---|---|
| SILICON | Si | 25% | SCANDIUM | Sc | 3.7 |
| ALUMINUM | Al | 9.3% | COBALT | Co | 4.8 |
| POTASSIUM | K | 4.8% | YTTERBIUM | Yb | 1.4 |
| MAGNESIUM | Mg | .83% | STRONTIUM | Sr | 240 |
| SULFUR | Si | 1.6% | BARIUM | Ba | 22.5 |
| IRON | Fe | 4.1% | GOLD | Au | .68 |
| CALCIUM | Ca | .23% | EUROPIUM | Eu | .49 |
| TITANIUM | Ti | .23% | NEODYMIUM | Nd | 20 |
| SODIUM | Na | 1.2 | CERIUM | Ce | 40 |
| MANGANESE | Mn | 150 | CESIUM | Cs | 183 |
| GALLIUM | Ga | 25 | THORIUM | Th | >100 |
| MOLYBDENUM | Mo | 61 | URANIUM | U | >100 |
| GERMANIUM | Ge | 25 | NICKEL | Ni | 60 |
| IODINE | I | 7 | BERYLLIUM | Be | .10 |
| BROMINE | Br | 5.2 | BISMUTH | Bi | 14.3 |
| TUNGSTEN | W | 8.1 | BORAN | B | 7 |
| HAFNIUM | Hf | 2 | CADMIUM | Cd | 1.12 |
| TANTALUM | Ta | .50 | CHLORIDE | Cl | 250 |
| ZIRCONIUM | Zr | 10 | COPPER | Cu | 2.2 |
| ARSENIC | As | .2 | FLUORIDE | Fl | 3.85 |
| ANTIMONY | Sb | 10.5 | LITHIUM | Li | 1.44 |
| SELENIUM | Se | 4.1 | MERCURY | Hg | .166 |
| ZINC | Zn | 20 | PALLADIUM | Pd | .74 |
| SAMARIUM | Sm | 3.5 | PHOSPHATE | Po4-P | 320 |
| HOLMIUM | Ho | 1.1 | PLATINUM | Pt | .08 |
| TERBIUM | Tb | .62 | RHODIUM | Rh | .44 |
| IRIDIUM | Ir | .51 | RUBIDIUM | Rb | 36.5 |
| LUTETIUM | Lu | .45 | SILVER | Ag | .3 |
| CHROMIUM | Cr | 70 | TELLURIUM | Te | .1 |
| LANTHANUM | La | 18 | THULIUM | Tm | .25 |
| RUTHENIUM | Ru | 7.8 | TIN | Sn | .44 |
| YTTRIUM | Y | 1.2 | VANADIUM | V | 8 |
| INDIUM | IN | .38 | DYSPROSIUM | Dy | 4.0 |
| LEAD | Pb | 15 | PRASEODYMIUM | Pr | 2.0 |
| NIOBIUM | Nb | 2.89 | THALLIUM | Tl | 10.0 |
| CARBON | C | .19 | RHENIUM | Re | 1.0 |
| HYDROGEN | H | .05 | ERBIUM | Er | 2.0 |
| NITROGEN | N | .03 | OXIGEN | O | .2 |

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A method of treating laminitis in a horse in need thereof, comprising administering to said horse an effective amount of a chelated trace mineral composition for promoting healthy hoof tissue, wherein said chelated trace mineral composition is prepared approximately with silicon 25%, scandium 3.7 parts/million by weight, aluminum 9.3, cobalt 4.8 parts/million by said weight, potassium 4.8%, ytterbium 1.4 parts/million by said weight, magnesium 0.83%, strontium 240 parts/million by said weight, sulfur 1.6%, barium 22.5 parts/million by said weight, iron 4.1%, gold 0.68 parts/million by said weight, calcium 0.23%, europium 0.49 parts/million by said weight, titanium 0.23%, neodymium 20 parts/million by said weight, sodium 1.2 parts/million by said weight, cerium 40 parts/million by said weight, manganese 150 parts /million by said weight, cesium 183 parts/million by weight, gallium 25 parts/million by said weight, thorium>100 parts/million by said weight, molybdenum 61 parts/million by said weight, uranium>100 parts/million by said weight, germanium 25 parts/million by said weight, nickel 60 parts/million by said weight, iodine 7 parts/million by said weight, beryllium 0.10 parts/million by said weight, bromine 5.2 parts/million by said weight, bismuth 14.3 parts/million by said weight, tungsten 8.1 parts/million by said weight, boron 7 parts/million by said weight, hafnium 2 parts/million by said weight, cadmium 1.12 parts/million by said weight, tantalum 0.50 parts/million by said weight, chloride 250 parts/million by said weight, zirconium 10 parts/million by said weight, copper 2.2 parts/million by said weight, arsenic 0.2 parts/million by said weight, fluoride 3.85 parts/million by said weight, antimony 10.5 parts/million by said weight, lithium 1.44 parts/million by said weight, selenium 4.1 parts/million by said weight, mercury 0.166 parts/million by said weight, zinc 20 parts/million by said weight, palladium 0.74 parts/million by said weight, samarium 3.5 parts/million by said weight, phosphate 320 parts/million by said weight, holmium 1.1 parts/million by said weight, platinum 0.08 parts/million by said weight, terbium 0.62 parts/million by said weight, rhodium 0.44 parts/million by said weight, iridium 0.51 parts/million by said weight, rubidium 36.5 parts/million by said weight, lutetium 0.45 parts/million by said weight, silver 0.3 parts/million by said weight, chromium 70 parts/million by said weight, tellurium 0.1 parts/million by said weight, lanthanum 18 parts/million by said weight, thulium 0.25 parts/million by said weight, ruthenium 7.8 parts million by said weight, tin 0.44 parts/million by said weight, yttrium 1.2 parts/million by said weight, vanadium 8 parts/million by said weight, indium 0.38 parts/million by said weight, dysprosium 4.0 parts/million by said weight, lead 15 parts/million by said weight, praseodymium 2.0 parts/million by said weight, niobium 2.89 parts/million by said weight thallium 10.0 parts/million by said weight, carbon 0.19 parts/million by said weight, rhenium 1.0 parts/million by said weight, hydrogen 0.05 parts/million by said weight, erbium 2.0 parts/million by said weight, nitrogen 0.03 parts/million by said weight, and oxygen 0.2 parts/million by said weight.

2. The method of claim 1, wherein said chelated trace mineral composition is administered with a dose of approximately 2 ounces, twice a day, for a period of 20 days, while maintaining a protein content of a horse diet to approximately 9%–10% of a total dietary intake per day.

3. The method of claim 2, wherein said chelated trace mineral composition is administered orally.

4. The method of reducing total dietary intake per day of a horse in need thereof, comprising administering to said horse an effective amount of a chelated trace mineral composition for promoting a reduction of daily grain intake, wherein said chelated trace mineral composition is prepared approximately with silicon 25%, scandium 3.7 parts/million by weight, aluminum 9.3%, cobalt 4.8 parts/million by said weight, potassium 4.8%, ytterbium 1.4 parts/million by said weight, magnesium 0.83%, strontium 240 parts/million-by said weight, sulfur 1.6%, barium 22.5 parts/million by said weight, iron 4.1%, gold 0.68 parts/million by said weight, calcium 0.23%, europium 0.49 parts/million by said weight, titanium 0.23%, neodymium 20 parts/million by said weight, sodium 1.2 parts/million by said weight, cerium 40 parts/million by said weight, manganese 150 parts/million by said weight, cesium 183 parts/million by weight, gallium 25 parts/million by said weight, thorium>100 parts/million by said weight, molybdenum 61 parts/million by said weight, uranium>100 parts/million by said weight, germanium 25 parts/million by said weight, nickel 60 parts/million by said weight, iodine 7 parts/million by said weight, beryllium 0.10 parts/million by said weight, bromine 5.2 parts/million by said weight, bismuth 14.3 parts/million by said weight, tungsten 8.1 parts/million by said weight, boron 7 parts/million by said weight, hafnium 2 parts/million by said weight, cadmium 1.12 parts/million by said weight, tantalum 0.50 parts/million by said weight, chloride 250 parts/million by said weight, zirconium 10 parts/million by said weight, copper 2.2 parts/million by said weight, arsenic 0.2 parts/million by said weight, fluoride 3.85 parts/million by said weight, antimony 10.5 parts/million by said weight, lithium 1.44 parts/million by said weight, selenium 4.1 parts/million by said weight, mercury 0.166 parts/million by said weight, zinc 20 parts/million by said weight, palladium 0.74 parts/million by said weight, samarium 3.5 parts/million by said weight, phosphate 320 parts/million by said weight, holmium 1.1 parts/million by said weight, platinum 0.08 parts/million by said weight, terbium 0.62 parts/million by said weight, rhodium 0.44parts/million by said weight, iridium 0.51 parts/million by said weight, rubidium 36.5 parts/million by said weight, lutetium 0.45 parts/million by said weight, silver 0.3 parts/million by said weight, chromium 70 parts/million by said weight, tellurium 0.1 parts/million by said weight, lanthanum 18 parts/million by said weight, thulium 0.25 parts/million by said weight, ruthenium 7.8 parts/million by said weight, tin 0.44 parts/million by said weight, yttrium 1.2 parts/million by said weight, vanadium 8 parts/million by said weight, indium 0.38 parts/million by said weight, dysprosium 4.0 parts/million by said weight, lead 15 parts/million by said weight, praseodymium 2.0 parts/million by said weight, niobium 2.89 parts/million by said weight, thallium 10.0 parts/million by said weight, carbon 0.19 parts/million by said weight, rhenium 1.0 parts/million by said weight, hydrogen 0.05 parts/million by said weight, erbium 2.0 parts/million by said weight, nitrogen 0.03 parts/million by said weight, and oxygen 0.2 parts/million by said weight.

5. The method of claim 4, wherein said chelated trace mineral composition is administered with a dose of approximately 2 ounces, once a day, for a period of 20 days, and with a dose of approximately 1–2 ounces per day after completing said period of 20 days, while maintaining a protein content of a horse diet to approximately 9%–10% of a total dietary intake per day.

6. The method of claim 5, wherein said chelated trace mineral composition is administered orally.

* * * * *